United States Patent [19]
Timbel

[11] Patent Number: 5,971,921
[45] Date of Patent: Oct. 26, 1999

[54] MEDICAL ALARM SYSTEM AND METHODS

[75] Inventor: Ned R. Timbel, Englewood, Colo.

[73] Assignee: Advanced Monitoring Devices, Inc., Littleton, Colo.

[21] Appl. No.: 09/096,298

[22] Filed: Jun. 11, 1998

[51] Int. Cl.[6] .................................................... A61B 5/00
[52] U.S. Cl. .......................................... 600/300; 128/904
[58] Field of Search .................................... 600/300, 301; 128/904, 903, 906; 607/60, 32

[56] References Cited

U.S. PATENT DOCUMENTS

| | | | |
|---|---|---|---|
| 5,467,773 | 11/1995 | Bergelson et al. | 128/904 |
| 5,544,661 | 8/1996 | Davis et al. | 128/904 |
| 5,729,203 | 3/1998 | Oka et al. | 128/904 |
| 5,772,586 | 6/1998 | Heinonen et al. | 128/904 |

OTHER PUBLICATIONS

AARP Product Report, Apr. 1992 "Table 1—PERS Product Reviewed by AARP".

*Primary Examiner*—Scott M. Getzow
*Attorney, Agent, or Firm*—Townsend and Townsend and Crew LLP

[57] ABSTRACT

The invention provides exemplary monitoring systems and methods for their use. In one exemplary method, a person is provided with a transmitter having an actuator. The actuator is operated to transmit a wireless signal of about 900 MHz. The signal from the transmitter is sensed with a receiver/caller unit which sends a digital signal over a telephone line to a monitoring center. This alerts the monitoring center of the actuation of the transmitter. A return signal is sent over the telephone line from the monitoring center to a speaker of the unit to verbally inquiring regarding the actuation of the transmitter.

21 Claims, 9 Drawing Sheets

MEDICAL ALARM SYSTEM AND METHODS

BACKGROUND OF THE INVENTION

This invention relates generally to the field of monitoring and in particular to the monitoring of individuals with health concerns. More specifically, the invention relates to the use of a wireless transmitter that may be operated by a user to notify a monitoring center of the need for assistance.

There is currently a widespread need for individuals with health problems to be monitored. For example, many elderly people live alone and may be unable to reach a telephone and dial an emergency number in the event of a medical emergency. Even if capable of operating a telephone, many elderly people do not wish to be tied to the immediate vicinity of a telephone in case assistance is needed.

A variety of monitoring systems have been proposed for such circumstances. For instance, some systems include transmitters which are operated to send signals to a receiver which in turn calls a monitoring center. However, such known prior art transmitters transmit relatively weak signals, typically near 300 MHz. Due to the relatively weak signal, the user must stay relatively close to the receiving unit or else the signal will be unable to be detected. As such, if the user moves away from the receiver and requires assistance, the monitoring center will be unable to be notified.

Another problem with many such monitoring systems is that they are not very robust. For example, many systems employ a conventional 9 volt backup battery which has a relatively short life. Hence, in the case of a power loss, the receiver will quickly become disabled. Such systems may also be unable to detect if the transmitter is operational. Further, such systems may be limited in their programming abilities to limit the functionality of the system.

Hence, it would be desirable to provide an improved monitoring system and methods for its use which has a transmitter with a relatively large operating range. The system should also be robust so that it can operate for a significant amount of time during a power outage. Further, the system should have a wide range of programming capabilities to improve its versatility.

SUMMARY OF THE INVENTION

The invention provides exemplary monitoring systems and methods for their use. In one exemplary method, a person is provided with a transmitter having an actuator. The actuator is actuated to transmit a wireless signal in the range from about 850 MHz to about 950 MHZ, and more preferably at about 900 MHz. The signal from the transmitter is sensed with a receiver/caller unit which in turn sends a digital signal over a telephone line to a monitoring center to alert the monitoring center of the activation of the transmitter. A return signal is sent over the telephone line from a monitoring center to a speaker in or on the unit to verbally inquire regarding the actuation in the transmitter. By providing an actuator which transmits a wireless signal of about 900 MHz, the strength of the signal may be greatly increased, thereby allowing a person to roam a considerable distance away from the receiver/caller unit while still being able to effectively transmit the signal.

In one particular aspect, the person is able to speak into the speaker to verbally communicate with the monitoring center. In this way, the monitoring center does not establish a verbal communication with the person, they may send for emergency help. In another aspect, a wireless test signal is periodically sent from the transmitter to the unit to test the charge of the battery in the transmitter. In this way, the unit may automatically and routinely test to see if the transmitter is operational. In still another aspect, a digital test signal is periodically sent over the telephone line from the unit to the monitoring center to allow the monitoring center to test the operability of the unit.

In still yet another aspect, the unit includes a lead-acid backup battery which provides extended life to the unit in the event of a power outage. The unit preferably includes a trickle charge circuit to periodically recharge the backup battery. In one particular aspect, the unit includes an on/off switch having an on position and an off position. The switch is placed in the off position when shipping the unit to prevent the discharge of power from the backup battery.

In still another aspect, the unit includes a programmable circuit board which may be programmed with telephone numbers for the monitoring center prior to shipping the unit to the person. In this way, the unit does not need to include an external key pad which may be difficult for the user to program. In yet another aspect, the unit includes a two-way voice circuit board which is programmed with two-way key codes which indicate, among others, a talk mode and a listen mode. The monitoring center is then notified with the two-way key codes so that they can use the codes to either talk or listen as appropriate.

The invention further provides an exemplary alarm system for a user needing medical assistance. The system comprises a portable transmitter having a hand actuated actuator. The transmitter produces a wireless signal of about 900 MHz upon operation of the actuator. The system further includes a receiver/caller unit which comprises a receiver to wirelessly receive the signal from the transmitter, circuitry coupled to the receiver to produce a digital signal that is transmittable over a telephone line to indicate actuation of the transmitter, a speaker to procure audible messages communicated over the telephone line, and a microphone to receive messages which are to be communicated over the telephone line. The alarm system is particularly advantageous in that it utilizes about a 900 MHz signal. In this way, a relatively strong signal may be produced so that a person carrying the transmitter may be at a significant distance away from the receiver/caller unit and still be able to notify the monitoring center in the event of an emergency.

In one aspect, the unit further includes a lead-acid backup battery. A trickle charge circuit is provided to periodically recharge the battery. The unit may also include a on/off switch having an on position and an off position. When in the off position, power is prevented from discharging from the battery.

In still another aspect, the unit preferably includes an electrical power cord which is adapted to couple the unit to a power source, such as a conventional 110 volt source. When plugged into a power source, the unit is operational regardless of the position of the on/off switch. In the event of a power outage, power is supplied from the backup battery.

In another aspect, the transmitter is configured to periodically send a test signal to the unit to confirm that the transmitter is operational. If the receiver does not receive a test signal within a predetermined amount of time, the unit produces a warning light indicating that the transmitter is not operational. In still another aspect, the unit includes a circuit board having a programmable memory device to allow telephone numbers, among other information, to be programmed into the unit. This information is preferably preprogrammed at the time of manufacturing so that the user will not need to understand how to program the unit. In one particular aspect, the programmable memory device is configured to be programmed with two-way key codes which indicate a talk mode and a listen mode. Such key codes are utilized by the monitoring center to communicate with the unit.

In one particularly preferable aspect, the unit is enclosed in a steel housing. In another aspect, the unit may include a light indicator to indicate receipt of the signal from the transmitter.

DETAILED DESCRIPTION OF THE SPECIFIC EMBODIMENTS

Figure 1:
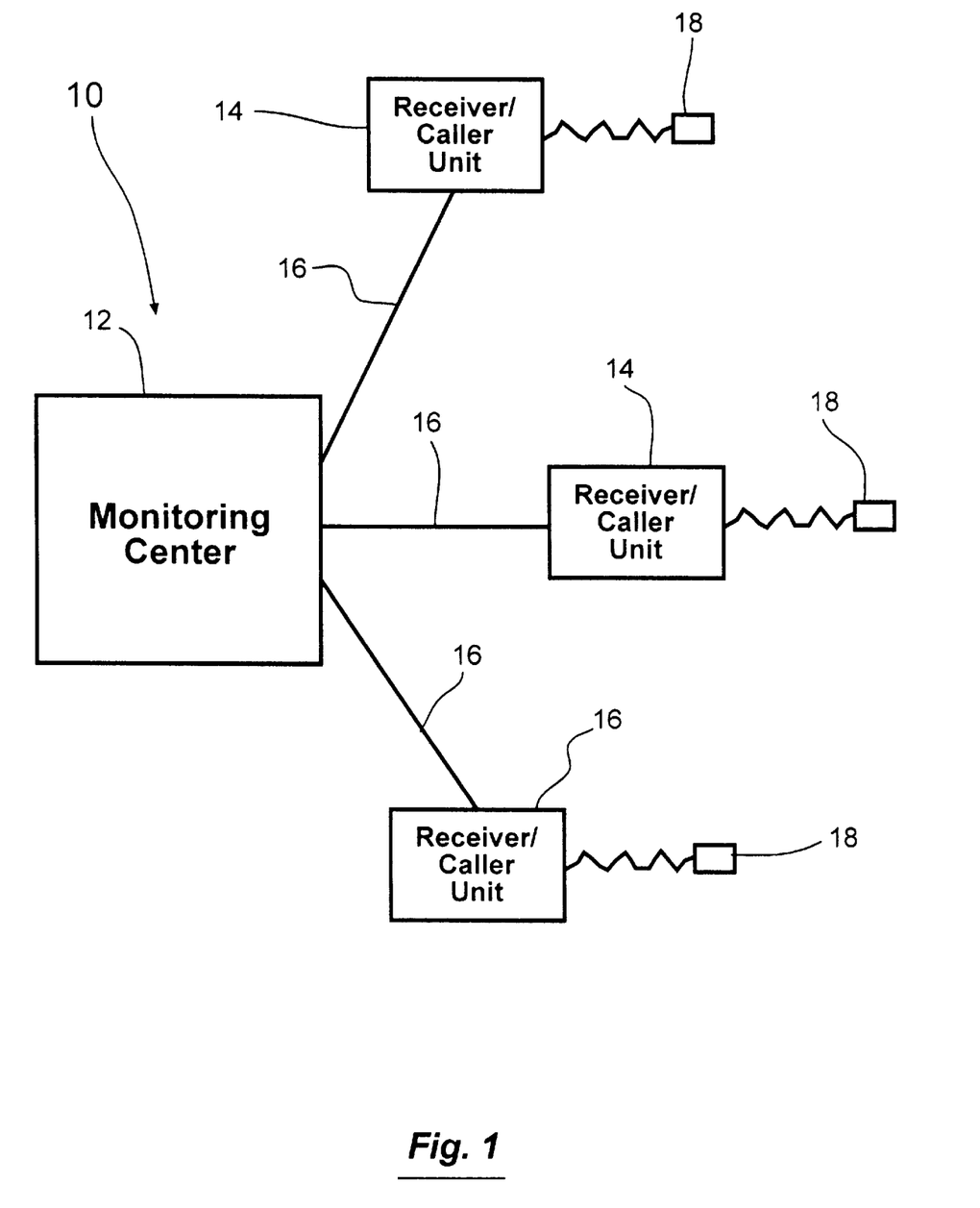
FIG. 1 is a schematic diagram of an exemplary monitoring system according to the invention.

Referring now to FIG. 1, an exemplary embodiment of a monitoring system 10 will be described. System 10 comprises a monitoring center 12, to which a plurality of receiver/caller units 14 are coupled via conventional telephone lines 16. Associated with each receiver/caller unit 14 is a wireless transmitter 18, which is typically worn by the person to be monitored.

In brief, monitoring system 10 operates by the user operating transmitter 18 in the event of a medical emergency. In turn, transmitter 18 sends a wireless signal which is received by receiver/caller unit 14. Upon receipt of the signal, receiver/caller unit 14 dials a telephone number of monitoring center 12 and establishes digital communication. An operator located in monitoring center 12 notes the alarm on a computer screen and attempts to establish two-way voice communication through receiver/caller unit 14. As described in greater detail hereinafter, receiver/caller unit 14 includes a speaker for amplifying the operator's voice within the user's residence. If voice communication can be established between the user and the monitoring center 12, an appropriate response may be discussed. However, if voice communication cannot be established within a predetermined time period, e.g., about three to five minutes, the operator at monitoring center 12 will follow protocol procedures to call for local medical assistance, typically in the form of an ambulance with paramedics. Following the alarm, receiver/caller unit 14 is automatically reset and is ready to receive another signal from transmitter 18.

One important feature of system 10 is that transmitter 18 is configured to send and receiver/caller unit 14 is adapted to receive wireless signals having a frequency in the range from about 850 MHz to about 950 MHz, more preferably in the range from about 902 MHz to about 928 MHz. The use of this frequency range is advantageous in that a relatively strong signal may be produced within this range to markedly increase the range of operability of transmitter 18. Typically, use of about a 900 MHz signal allows the user to have an operating range of greater than 500 feet from unit 14 (when the user is located within a building which has walls which hinder transmission of the signal). When located outside, the user may be located at approximately ¼ mile and still be able to effectively transmit a signal to unit 14.

Another important feature of system 10 is its ability to routinely monitor itself to make sure that each of the elements are operational. For example, transmitter 18 is configured to periodically, e.g. about every 1½ minutes, send a test signal to unit 14. If unit 14 does not detect the test signal from transmitter 18 within a predetermined amount of time, e.g. about 5 minutes, unit 14 will indicate that transmitter 18 may not be operational. Receiver/caller unit 14 is further configured to periodically, e.g. about once a month, send a test signal to monitoring center 12. Monitoring center 12 is sent a special signal so that it understands the message to be a test signal. If the test signal is not received by monitoring center 12, it will know that a problem exists with the operability of unit 14 and will take the appropriate steps to notify the user of the problem.

Figure 2:
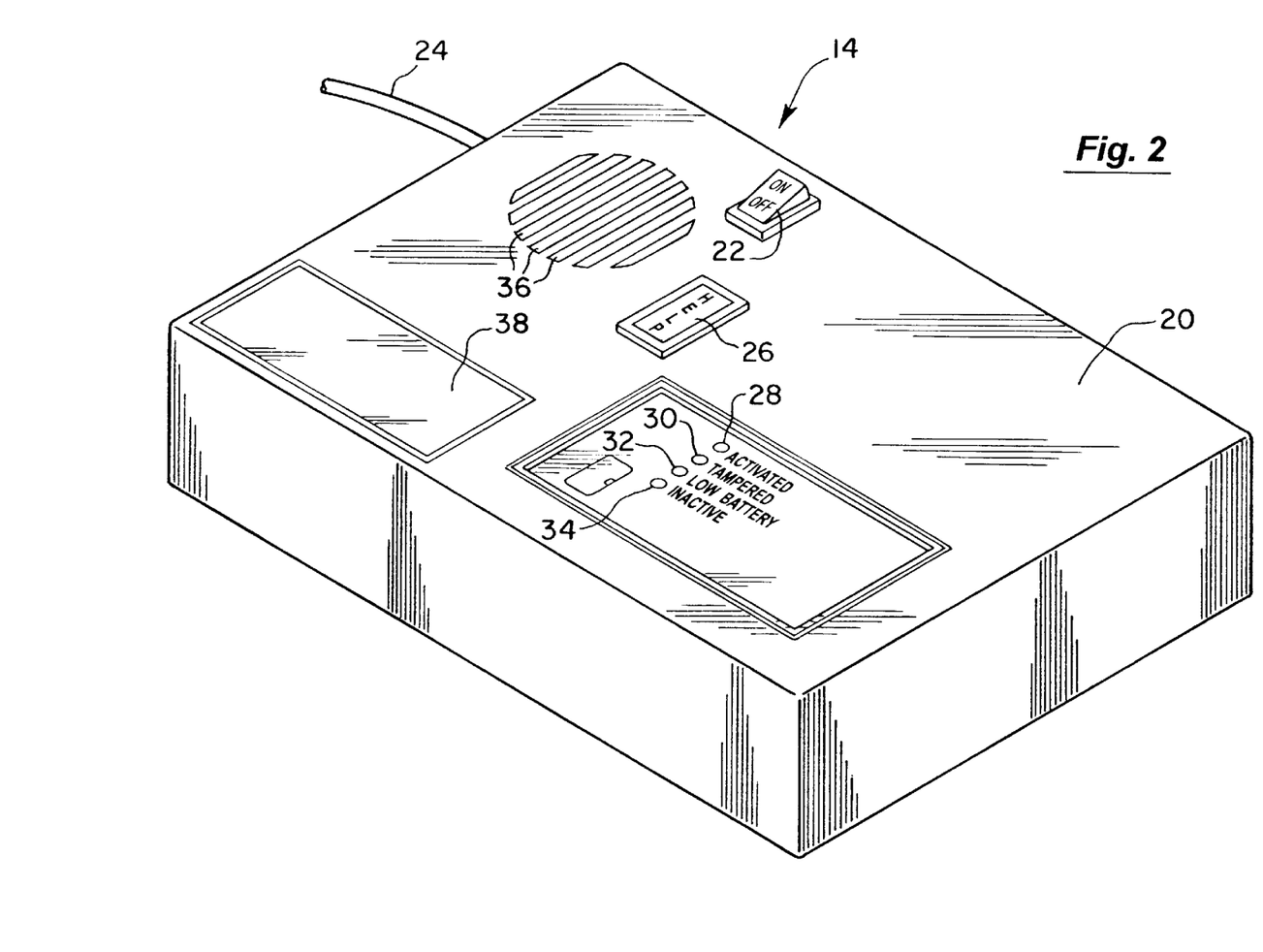
FIG. 2 is a perspective view of an exemplary receiver/caller unit of the system of FIG. 1 according to the invention.
Figure 3:
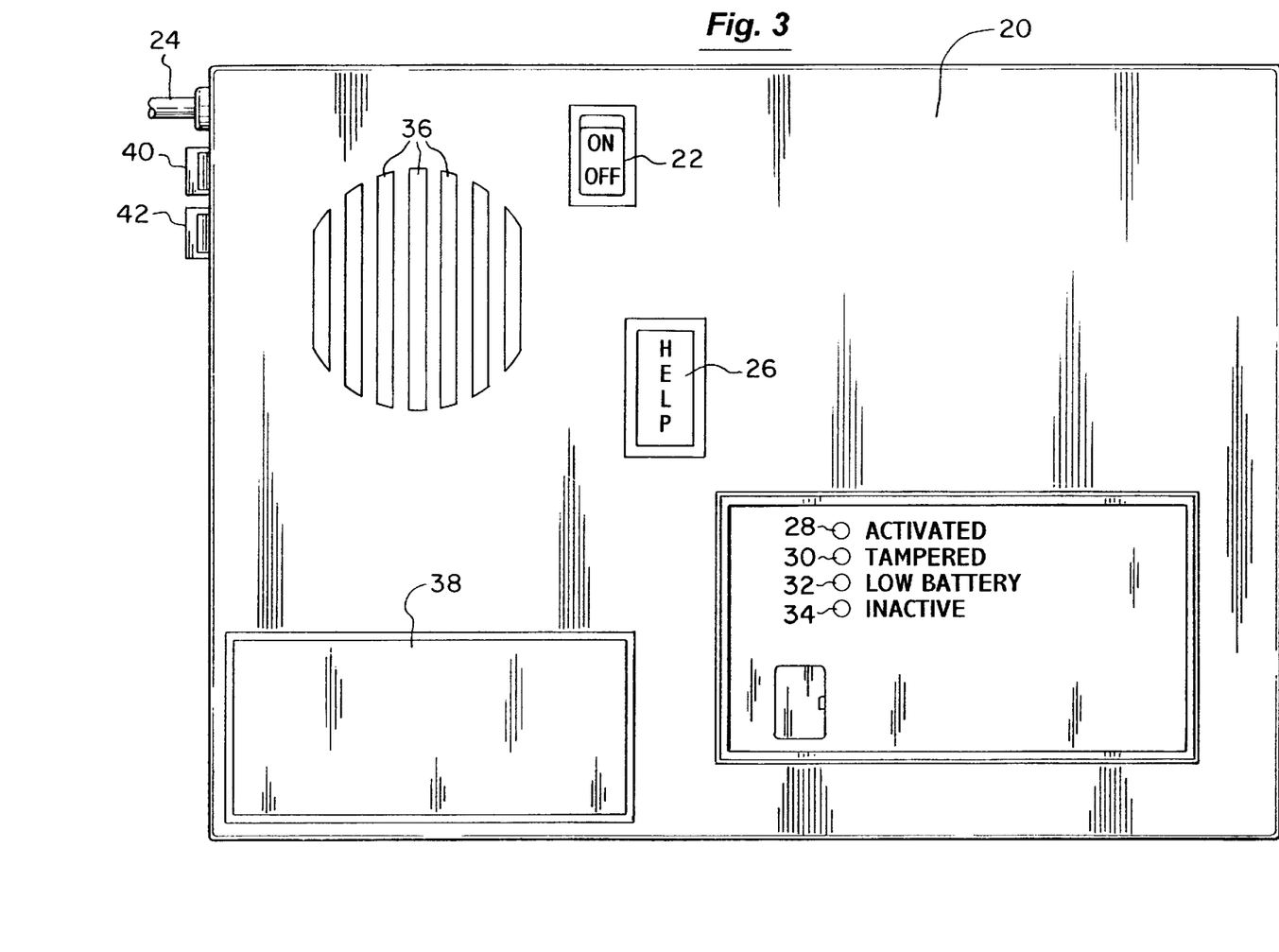
FIG. 3 is a top plan view of the unit of FIG. 2.
Figure 4:
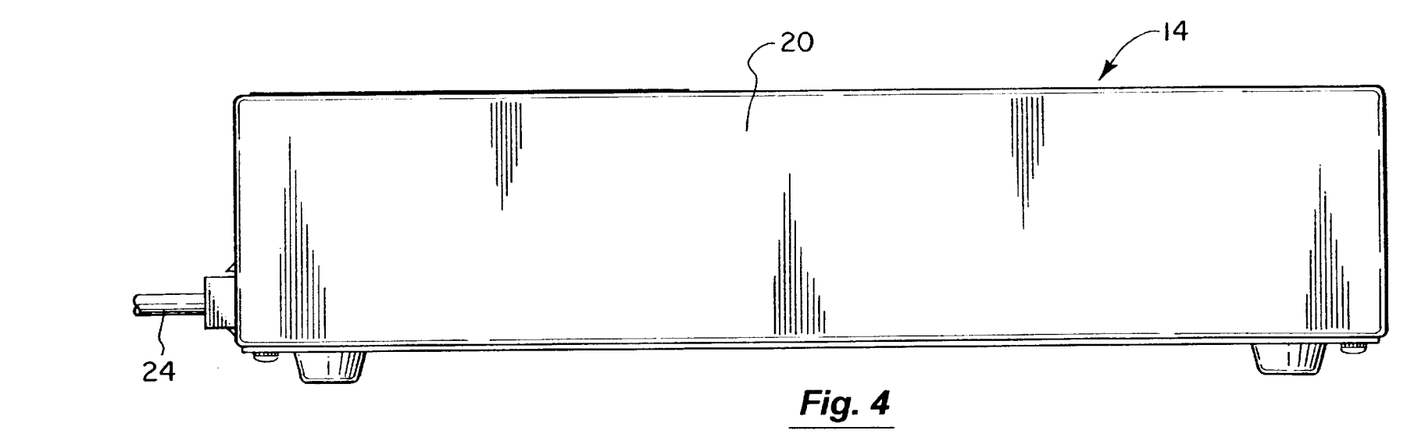
FIG. 4 is a front elevational view of the unit of FIG. 2.
Figure 5:
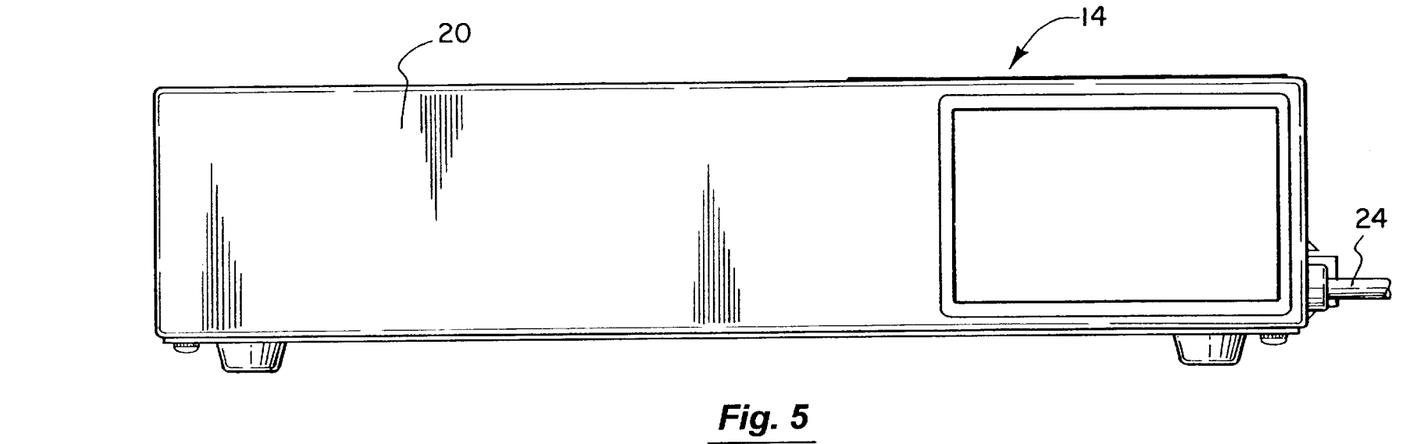
FIG. 5 is a rear elevational view of the unit of FIG. 2.

Referring now to FIGS. 2–8, construction of receiver/caller unit 14 will be described in greater detail. Unit 14 is constructed of a durable housing 20 which is preferably constructed of metal to provide protection to the components held within housing 20. As best shown in FIGS. 2 and 3, unit 14 further includes an on/off switch 22 whose primary function is to prevent the discharge of power from a backup battery of unit 14 during shipping. In this way, a switch is provided to ensure the operability of the backup battery after shipping and installation. Once installed, switch 22 is placed to an on position where the backup battery is operational to supply power to unit 14 in the event of a power outage. As best shown in FIGS. 3 and 4, a power cable 24 having a plug (not shown) is provided to allow unit 14 to be electrically coupled to a conventional power outlet, such as a 110 VAC outlet, to supply power to unit 14.

Placed on unit 14 is a help button 26. As its name suggests, button 26 may be depressed to cause unit 14 to establish digital communication with monitoring center 12 (see FIG. 1) in a manner similar to that when transmitter 18 (see FIG. 1) is operated. In this way, the user is provided with another option for attempting to establish communication with the monitoring center.

Unit 14 further includes a plurality of warning lights, including an activated light 28, a tampered light 30, a low battery light 32, and an inactive light 34. Activated light 28 is lighted when transmitter 18 (see FIG. 1) or help button 26 is depressed to indicate that a signal has been received by unit 14. Tampered light 30 may be activated in the event that any of the components within transmitter 18 are tampered with by an unauthorized person. Low battery light 32 is lighted when a weak test signal from transmitter 18 (see FIG. 1) is received and detected by unit 14. Typically, low battery light 32 will be lighted when the battery within the transmitter has approximately one week of life remaining. Inactive light 34 is lighted when the transmitter fails to transmit its test signal to unit 14.

Disposed in housing 20 are voice communication holes 36 through which a speaker within housing 20 may verbally communicate and through which a user may speak into to pass verbal messages into a microphone within housing 20. Still referring to FIGS. 2 and 3, a label 38 may optionally be placed on housing 20 to provide various labeling information, such as the name and trademark of the manufacturer.

Figure 6:
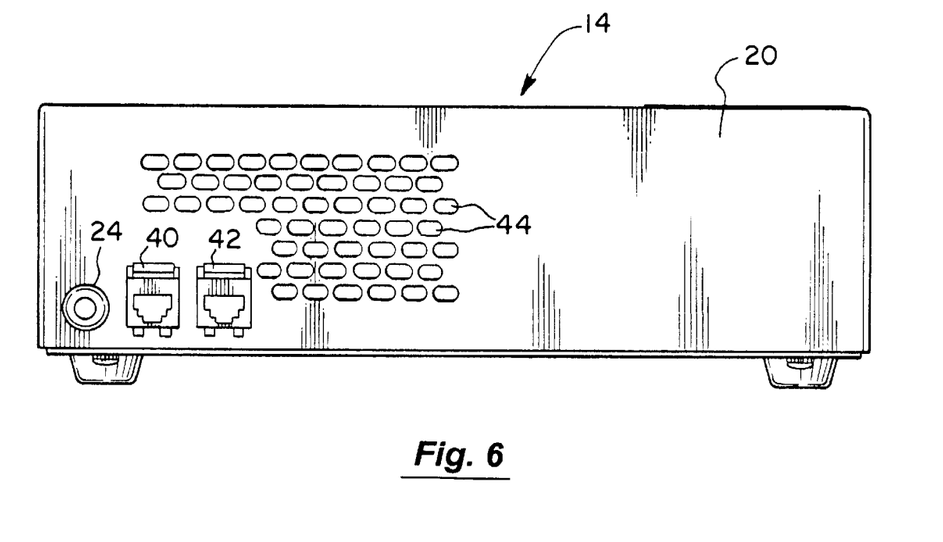
FIG. 6 is a left side elevational view of the unit of FIG. 2.
Figure 7:
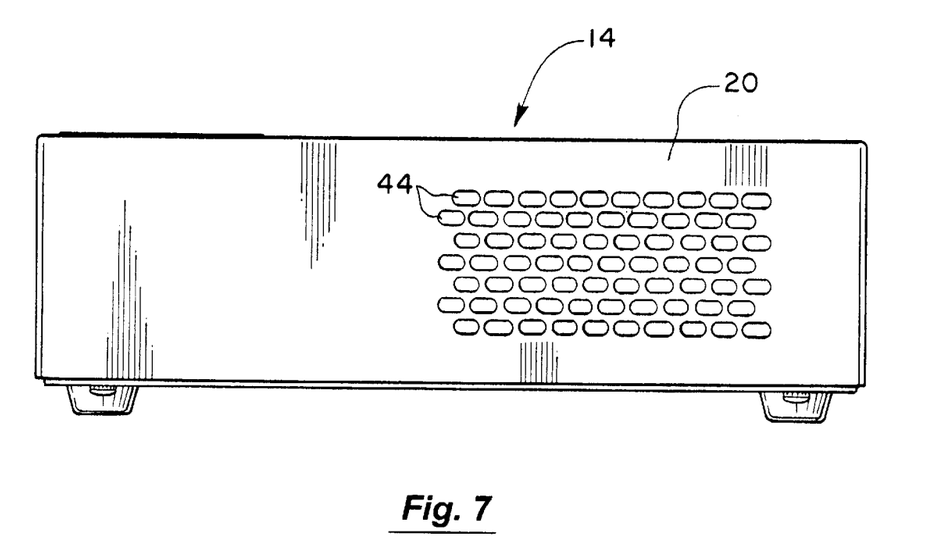
FIG. 7 is a right side elevational view of the unit of FIG. 2.
Figure 8:
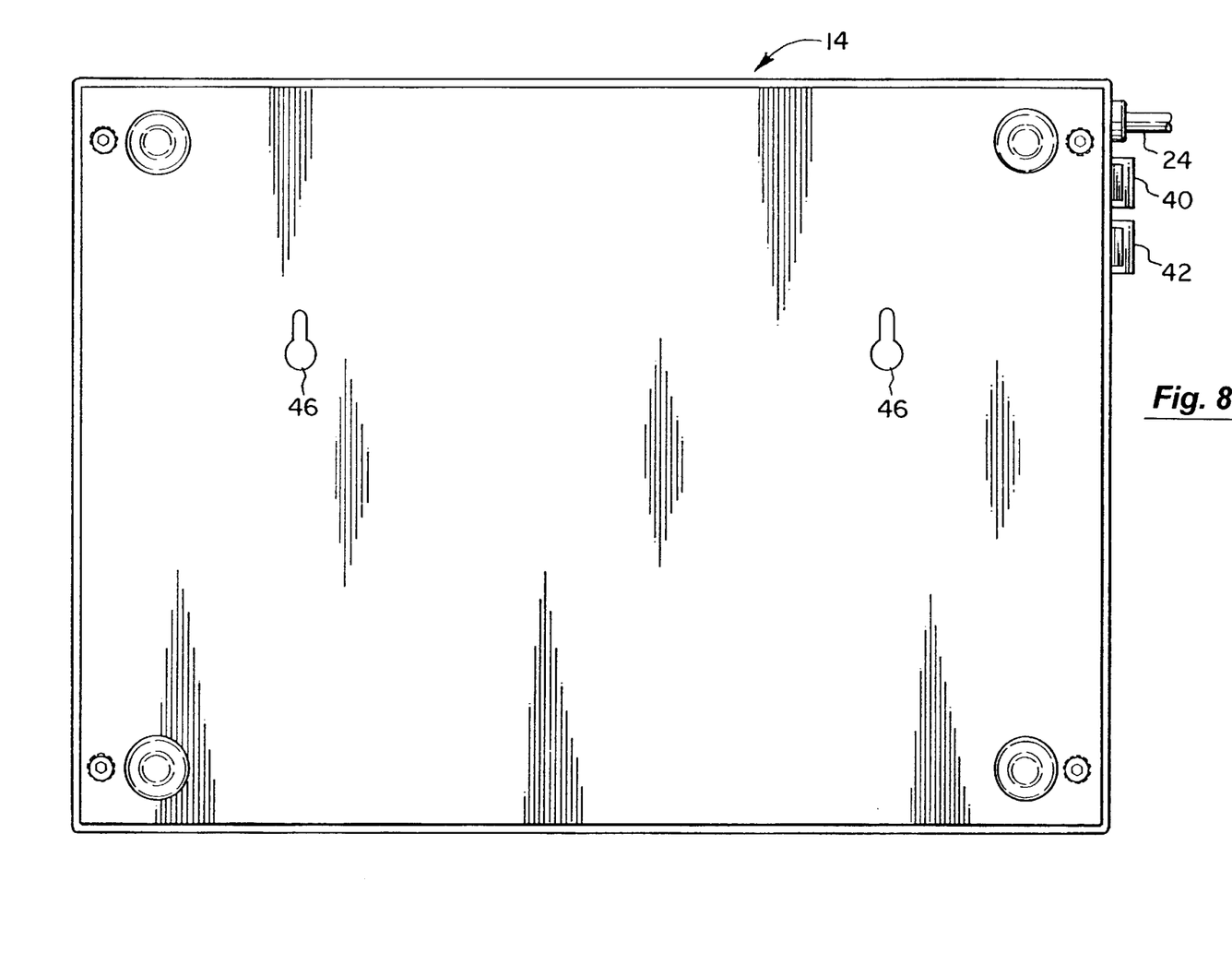
FIG. 8 is a bottom plan view of the unit of FIG. 2.

As best shown in FIGS. 3 and 6, a pair of phone jacks 40 and 42 are coupled to housing 20. One of the jacks allows unit 14 to be coupled to the monitoring center via a telephone line. The remaining jack serves as an extra jack that allows the user's telephone to be coupled to unit 14, it being appreciated that the jacks are interchangeable so that either can be connected to the monitoring center or the user's telephone. Use of jacks 40 and 42 is therefore advantageous in that if the user's room in which unit 14 is to be placed includes only one telephone jack, the user is still able to use his telephone by coupling it to the unused jack 40 or 42. As shown in FIGS. 6 and 7, a plurality of holes 44 are provided in housing 20 to provide adequate ventilation to the electrical components within housing 20. As best shown in FIG. 8, a pair of mounting holes 46 may optionally be included in housing 20 to allow unit 14 to be hung from a wall.

Figure 9:
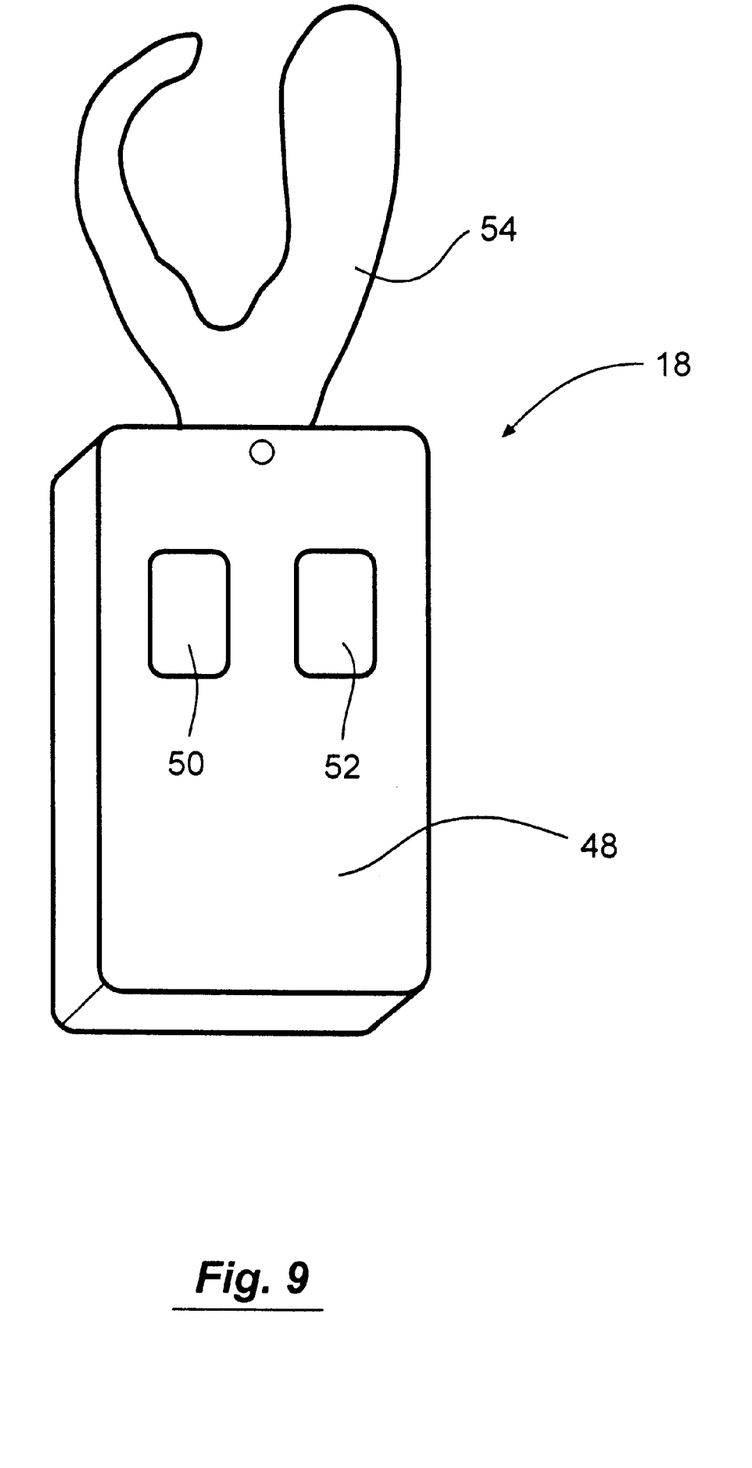
FIG. 9 is a top perspective view of an exemplary transmitter of the system of FIG. 1 according to the invention.

Referring now to FIG. 9, construction of transmitter 18 will be described in greater detail. Transmitter 18 comprises a housing 48 having a pair of actuator buttons 50 and 52. A breakaway necklace 54 is coupled to housing 48 and allows transmitter 18 to conveniently be worn around the user's neck. Alternatively, housing 48 may include a belt clip to attach transmitter 18 to the user's belt.

To operate unit 18, buttons 50 and 52 are simultaneously depressed. When depressed, a signal in the range from about 850 MHz to about 950 MHz is transmitted so that it may be detected by unit 14. Alternatively, only a single actuation button may be employed which may be depressed to transmit the wireless signal. As previously described, use of a signal of about 900 MHz is advantageous in that the strength of the signal may be increased to greatly increase the operating range. One particularly preferred frequency range is about 902 MHz to about 928 MHz. When operating within this range, transmitter 18 is configured to comply with part 15 of the FCC Rules. An exemplary transmitter which may be used with the invention is a transmitter which is part of a receiver unit, model FA-2600-WH-In Touch, commercially available from Inovonics, Boulder, Colo.

Transmitter 18 preferably operates using a 3.0 volt lithium battery, which has approximately a four-year life. As previously mentioned, transmitter 18 regularly transmits test signals to the receiver/caller unit to confirm that the battery is still charged and that transmitter 18 is operational.

Figure 10:
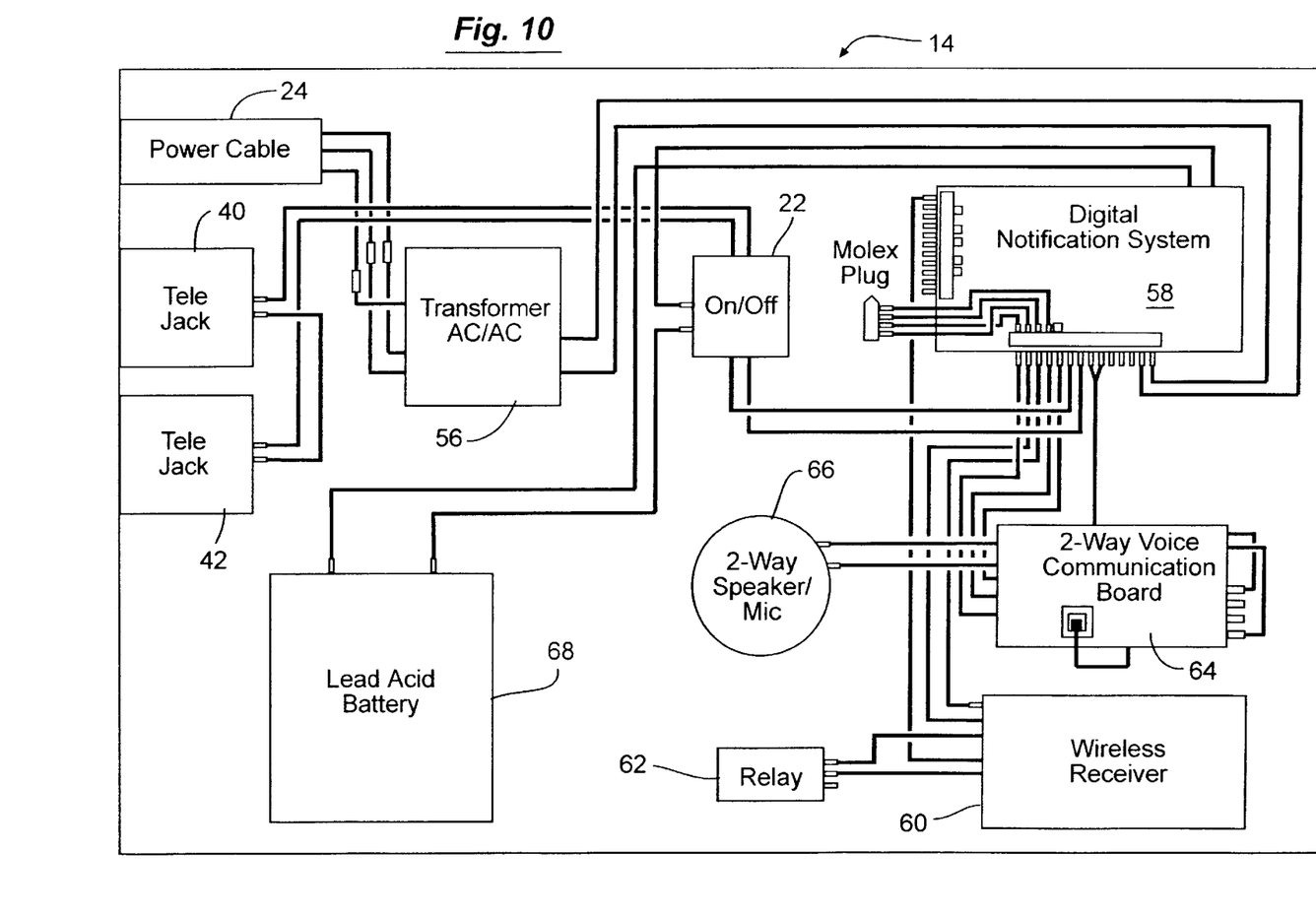
FIG. 10 illustrates a schematic diagram of the circuitry of the receiver/caller unit of the FIG. 2 according to the invention.

Referring now to FIG. 10, the electrical circuitry within unit 14 will be described schematically. As previously described, 110 volt alternating current is supplied to unit 14 through a power cable 24. The current is transformed to 12 volt alternating current by a transformer 56. An exemplary transformer for converting the current is an Edwards ED-596(12 VAC 32 VA Trans.) transformer, commercially available from ADI, Denver, Colo.

Transformer 56 supplies current to a digital notification system 58, which comprises a circuit board having circuitry to place a telephone call via jack 40 or 42 to the monitoring center upon receipt of a wireless signal from a transmitter. An exemplary digital notification system is a model XL-2S Main Board, commercially available from Fire Burglary Instruments, Inc., Syosset, N.Y.

Wireless receiver 60 is coupled to digital notification system 58 and receives wireless signals from transmitter 18 (see FIG. 9). In this way, when transmitter 18 is actuated, wireless receiver 60 will detect the transmitted signal and will send a signal to digital notification system 58 indicating actuation of the transmitter. As previously described, the transmitter is configured to routinely send test signals to wireless receiver 60 so that wireless receiver 60 can determine if the transmitter is operational. If the test signal is not received within predetermined amount of time, wireless receiver 60 will actuate low battery light 32 or inactive light 34 (see FIG. 3) as appropriate. Upon actuation of a transmitter by a user, receiver 60 will also light activated light 28 (see FIG. 3) to indicate that a signal has been received. An exemplary wireless receiver is an FA-2600-WH-In Touch Receiver, commercially available from Inovonics, Boulder, Colo.

Wireless receiver 60 is further coupled to a relay 62, which in turn is coupled to help button 26 (see FIG. 3). In this way, when help button 26 is depressed, relay 62 is actuated to send signal to wireless receiver 60. In turn, wireless receiver 60 sends a signal to digital notification system 58 so that the monitoring center may be called.

Further coupled to digital notification system 58 is a two-way voice communication board 64, which allows for two-way verbal communication between the monitoring center and the user. An exemplary communication board 64 is a model ETE-203N Two-Way voice Module, commercially available from Alarm Verification Products, Inc., Broomfield, Colo. Coupled to communication board 64 is a two-way speaker/microphone 66. Speaker/microphone 66 is aligned with holes 44 (see FIG. 3) to allow the user to speak into speaker/microphone 66 and to allow the monitoring center to communicate with the user through speaker/microphone 66.

One exemplary feature of communication board 64 is that it may be pre-programmed with two-way key codes to facilitate communication between the monitoring center and the user. For example, communication board 64 may be programmed with the following key codes: talk, listen, extend, and end. These key codes are provided to the monitoring center and are used by the monitoring center to facilitate a verbal discussion. For example, when the communication center wishes to speak to the user, the talk key code is entered. When the communication center needs to listen, the listen key code is entered. An exemplary two-way speaker/microphone which may be employed by the invention is a Model 40/1333 speaker, commercially available from Radio Shack.

Unit 13 further includes a backup lead acid battery 68 which is coupled to digital notification system 58. In this way, if power from power cable 24 becomes unavailable, unit 14 may remain operational because of the supply of power from backup battery 68. A preferable battery comprises a lead acid PS-1242 battery, commercially available from ADI, Denver, Colo. Use of the lead acid battery is particularly advantageous in that it has a relatively long life. For example, unit 14 may be operated for up to about 24 hours in the absence of power from power cable 24.

As previously described, on/off switch 22 is provided to prevent the discharge of power from backup battery 68 when in the off position. In this way, unit 14 may be shipped while switch 22 is in the off position to prevent draining of power from backup battery 68. When ready for operation, switch 22 is placed in the on position so that if power from power cable 24 is stopped, unit 14 may operate from power supplied by backup battery 68. Regardless of the position of on/off switch 22, power will always be supplied to digital notification system 58 if power is being supplied from power cable 24. Digital notification system 58 further includes a trickle recharge circuit which supplies current to lead acid battery 68 when power cable 24 is plugged into a socket to constantly recharge battery 68.

Also coupled to digital notification system 58 is a molex plug 70 to which an external keyboard may be coupled so that digital notification system 58 may be pre-programmed prior to shipping. Use of plug 70 is therefore advantageous in that programming may be done in the factory and unit 14 may be shipped without including a keyboard which would otherwise be required to program unit 14. An exemplary keypad which may be employed to program digital notification system 58 at the factory comprises a Model XL 6805 SM Key pad, commercially available from Fire Burglary Instruments, Inc., Syosset, N.Y. A variety of information may be pre-programmed into digital notification system 58 so that it may properly communicate with the monitoring center. This information is stored in a nonvolatile memory so that the appropriate information will not be lost in the event of a power outage. Merely by way of example, digital notification system 58 may be programmed with the following information: one or more telephone numbers for contacting the monitoring center, the dialer format, the monitoring center receiver type, the message length from the monitoring center, a ring-back from the monitoring center following a test, an entry delay time by which the monitoring center will contact emergency personnel if no response is received, a test interval which allows for the transmission of a test code to the central station at the interval selected in the absence of any other signal, a trigger function which allows for two-way voice communication, account numbers used by the monitoring center, power-off codes, low battery codes, test codes for the monitoring center, restore codes, and the like.

In summary, unit 14 operates by detecting a wireless signal from a transmitter with wireless receiver 60 (or by receiving a signal from relay 62). In turn, a signal is sent from receiver 60 to digital notification system 58. Based on the preprogrammed codes in digital notification system 58, the phone number of the monitoring center is dialed to establish digital communication between digital notification system 58 and the monitoring center. Once digital communication is established, the monitoring center attempts to establish verbal communication with the user by speaking over two-way speaker/microphone 66 using the preprogrammed two-way key codes in communication board 64. If the user is able, the user may speak into microphone 66 to establish verbal communication with the monitoring center. If verbal communication is not established within a predetermined time, the monitoring center sends for emergency help as appropriate.

Figure 11:
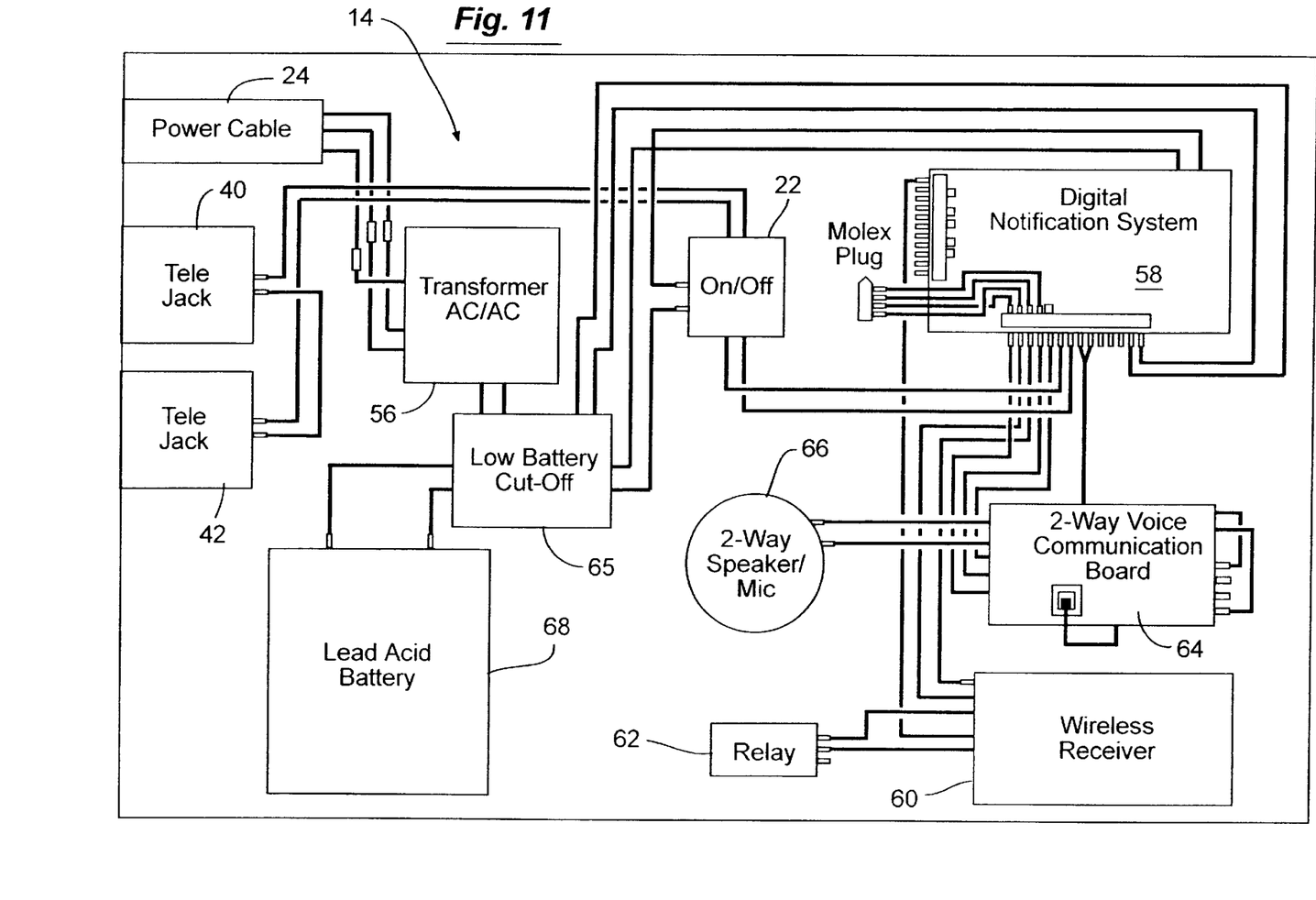
FIG. 11 illustrates an alternative embodiment of the schematic diagram of FIG. 10 having a low battery cut-off circuit according to the invention.

As shown in FIG. 11, unit 14 may be modified to include a low battery cut-off circuit 65 which is disposed between battery 68 and digital notification system 58. Cut-off circuit 65 is configured to electrically disconnect battery 68 from digital notification system 58 when the voltage of battery 68 falls below a threshold value, such as about 8.5V. Hence, cut-off circuit 65 provides a way to protect against deep discharge of battery 65 when unit 14 is not plugged in to a power supply. Moreover, since battery 68 is not allowed to discharge below the threshold voltage, once unit 14 is again connected to a power supply, battery 68 will be quickly recharged. When cut-off circuit 65 is included in unit 14, on/off switch 22 may optionally be removed. An exemplary cut-off circuit is a LB-100 low battery cut-off module, commercially available from Stealth Laboratories, Hickory, N.C.

Although the foregoing invention has been described in some detail by way of illustration and example, for purposes of clarity of understanding, it will be appreciated that certain changes and modifications may be practiced within the scope of the appended claims.

What is claimed is:

1. A monitoring method comprising:

providing a person with a transmitter having an actuator;

operating the actuator to transmit a wireless signal in the range from about 850 MHz to about 950 MHz;

sensing the signal from the transmitter with a receiver/caller unit;

sending a digital signal from the unit over a telephone line to a monitoring center to alert the monitoring center of the actuation of the transmitter; and sending a return signal over the telephone line from the monitoring center to a speaker of the unit to verbally inquire regarding the actuation of the transmitter.

2. A method as in claim 1, further comprising speaking into the speaker to verbally communicate with the monitoring center.

3. A method as in claim 1, further comprising periodically sending a wireless test signal from the transmitter to the unit to test the charge of a battery in the transmitter.

4. A method as in claim 1, further comprising periodically sending a digital test signal over the telephone line from the unit to the monitoring center.

5. A method as in claim 1, wherein the unit includes a lead acid back-up battery, further comprising periodically recharging the back-up battery with a trickle charge circuit, and further comprising electrically disconnecting the back-up battery from the unit when the voltage of the back-up battery falls below a threshold value.

6. A method as in claim 5, wherein the unit includes an on/off switch having an on position and an off position, and further comprising placing the switch in the off position when shipping the unit to prevent the discharge of power from the back-up battery.

7. A method as in claim 1, wherein the unit includes a programmable circuit board, and further comprising programming the circuit board with telephone numbers for the monitoring center prior to shipping the unit to the person.

8. A method as in claim 1, wherein the unit includes a two-way voice circuit board, further comprising programming the circuit board with two way key codes which indicate a talk mode and a listen mode, and further comprising communicating to the monitoring center the two-way key codes.

9. An alarm system for a user needing medical assistance, the system comprising:

a portable transmitter having a hand actuated actuator, the transmitter producing a wireless signal in the range from about 850 MHz to about 950 MHz upon operation of the actuator;

a receiver/caller unit comprising a receiver to wirelessly receive the signal from the transmitter, circuitry coupled to the receiver to produce and transmit a digital signal that is transmittable over a telephone line to indicate actuation of the transmitter, a speaker to produce audible messages communicated over the telephone line, and a microphone to receive verbal messages which are to be communicated over the telephone line.

10. A system as in claim 9, wherein the unit further includes a lead acid back-up battery.

11. A system as in claim 10, wherein the unit further includes a trickle charge circuit to recharge the battery, and a cut-off circuit to electrically disconnect the back-up battery from the unit when the voltage of the back-up battery falls below a threshold value.

12. A system as in claim 10, wherein the unit further comprises an on/off switch having an on position and an off position, wherein power is prevented from discharging from the battery only when the switch is in the off position.

13. A system as in claim 12, further comprising an electrical power cord which is adapted to couple the unit to a power source.

14. A system as in claim 13, wherein the unit is configured to be operational when the plug is coupled to a power source regardless of the position of the on/off switch.

15. A system as in claim 9, wherein the transmitter is configured to periodically send a test signal to the unit to confirm that the transmitter is operational.

16. A system as in claim 15, wherein the unit produces a warning light if the receiver does not receive the test signal within a predetermined amount of time.

17. A system as in claim 9, wherein the unit further includes a circuit board having a programmable memory device to allow telephone numbers to be programmed into the unit.

18. A system as in claim 17, wherein the programmable memory device is configured to be programmed with two-way key codes which indicate a talk mode and a listen mode.

19. A system as in claim 9, wherein the unit includes a steel housing.

20. A system as in claim 9, wherein the unit includes a light indicator to indicate receipt of the signal from the transmitter.

21. An alarm system for a user needing medical assistance, the system comprising:

a portable transmitter having a hand actuated actuator, the transmitter producing a wireless signal upon operation of the actuator;

a receiver/caller unit comprising a receiver to wirelessly receive the signal from the transmitter, circuitry coupled to the receiver to produce and transmit a digital signal that is transmittable over a telephone line to indicate actuation of the transmitter, a speaker to produce audible messages communicated over the telephone line, and a microphone to receive available messages which are to be communicated over the telephone line, wherein the unit further comprises an on/off switch having an on position and an off position, and an electrical power cord which is adapted to couple the unit to a power source, wherein the unit is configured to be operational when the plug is coupled to a power source regardless of the position of the on/off switch;

wherein the unit includes a battery, and wherein power is prevented from discharging from the battery only when the switch is in the off position; and wherein the transmitter produces a wireless signal of about 900 MHz upon operation of the actuator.

* * * * *